United States Patent
Rush

(10) Patent No.: US 6,660,323 B1
(45) Date of Patent: Dec. 9, 2003

(54) METHOD FOR TREATING CATTAIL BLOSSOMS

(76) Inventor: Ronald Earl Rush, 2456 Pattie, Wichita, KS (US) 67216

( * ) Notice: Subject to any disclaimer, the term of this patent is extended or adjusted under 35 U.S.C. 154(b) by 0 days.

(21) Appl. No.: 10/134,742

(22) Filed: Apr. 29, 2002

Related U.S. Application Data

(60) Provisional application No. 60/287,806, filed on Apr. 30, 2001.

(51) Int. Cl.$^7$ .............................. B05D 1/00; B05D 1/18
(52) U.S. Cl. ...................... 427/4; 427/230; 427/430.1; 427/439; 428/15; 428/17; 428/24
(58) Field of Search .................. 427/4, 230, 430.1, 427/439; 428/15, 17, 24

(56) References Cited

U.S. PATENT DOCUMENTS 2,606,843 A * 8/1952 Fessenden ................. 427/4
4,349,459 A * 9/1982 Romero-Sierra et al. ... 504/115

* cited by examiner

*Primary Examiner*—Shrive P. Beck
*Assistant Examiner*—Jennifer Kolb Michener
(74) *Attorney, Agent, or Firm*—Robert Blinn

(57) ABSTRACT

The present invention is a method for treating a cattail blossom. A cattail blossom is soaked in a thinned adhesive mixture. When dry, the resulting treated blossom does not burst and can be used for a very long period of time as a decorative item.

12 Claims, 1 Drawing Sheet

METHOD FOR TREATING CATTAIL BLOSSOMS

CROSS REFERENCES TO RELATED APPLICATIONS

This application claims the benefit of U.S. Provisional Patent Application No. 60/287,806 filed Apr. 30, 2001.

FIELD OF THE INVENTION

This invention relates to a method for stabilizing a cattail blossom in a condition having a natural appearance and texture so that the cattail blossom does not burst and shed seeds but remains intact for an extended period of time.

BACKGROUND OF THE INVENTION

The Cattail is a wild plant that grows in swamps and marshes throughout temperate parts of the Northern Hemisphere. On the Pacific Coast, cattails are known as tule-reeds. Cattails occur in a number of varieties. The Common Cattail (*Typha latifolia*) grows to about ten to thirteen feet in height and has large blossoms. The Narrowleaf Cattail (*Typha angustifolia*) is a smaller variety that grows to about six feet in height and has a blossom that is five to eight inches in length and one-half to three quarters of an inch in diameter. Other varieties include the Southern Cattail (*Typha domingensis*) and the Blue Cattail (*Typha Glauca*).

Florists typically use the blossoms of the smaller Narrowleaf Cattail (Typha angustifolia) as decorative items or to decorate floral arrangements. Cattails can be harvested throughout the United States in wetland areas between June and October. Each year, a large supply of cattail blossoms becomes available to florists in late summer.

Unfortunately, cattail blossoms have one significant disadvantage for florists and their customers. Nature did not design cattail blossoms to be a decorative item but rather a means for broadcasting seeds. A cattail blossom is a generally cylindrical mass of tightly packed seeds containing between 100,000 and 300,000 seeds. These seeds have bristly, silky hairs that aid in wind dispersal. At maturity and usually under dry conditions, a cattail blossom will burst and release its seeds. A cattail blossom will usually burst sometime in the late Fall or early Winter. Although this is a highly effective means for dispersing many thousands of seeds, this significantly reduces the value and usefulness of cattail blossoms as a decorative item.

SUMMARY OF THE INVENTION

Accordingly, a primary object of the subject invention is to provide a method for treating cattail blossoms so that they do not burst under dry conditions and remain intact indefinitely. Another object of the subject invention is to provide a method for treating cattail blossoms so that they have a natural appearance and texture even when treated.

These objects may be attained by mixing a combination of mineral spirits, paint thinner and adhesive, maintaining that mixture at a warm temperature, dipping a cattail blossom into the mixture until it is completely soaked, removing the cattail blossom from the mixture and then drying the cattail blossom.

The above described process is easy and inexpensive to conduct and adds greatly to the value of cattail blossoms in the florist market. Cattails thus treated can now be painted or decorated with ornamental designs such as university logos, business logos or animal designs. Because cattails treated with the above described process will maintain their shape and appearance indefinitely, the cost and effort of decorating and painting such ornamental cattails is acceptable.

BRIEF DESCRIPTION OF THE DRAWINGS

The invention and its many attendant objects and advantages will become better understood upon reading the following description of the preferred embodiment in conjunction with the following drawings, wherein.

DETAILED DESCRIPTION

Figures 1, 2:
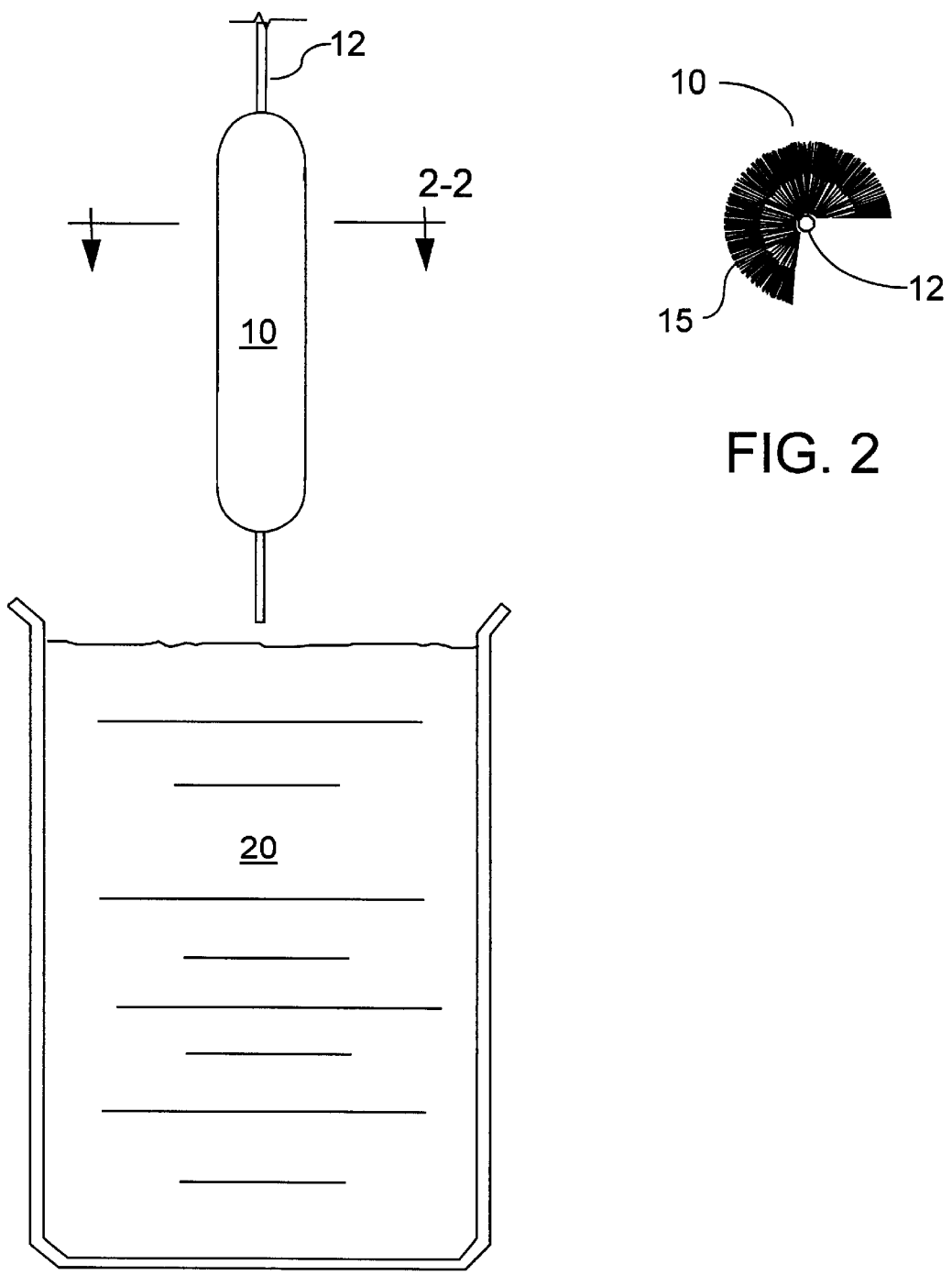
FIG. 1 is a side view of a cattail suspended over a vessel containing a treatment mixture.
FIG. 2 is a cross sectional view of a cattail taken from plane 2—2 of FIG. 1 enlarged at a two to one scale in relation to FIG. 1.

Turning now to the drawings, wherein like reference numerals designate identical or corresponding parts, and more particularly to FIG. 1 thereof, a cattail blossom 10 is shown hanging from its stem 12 in relation to a container of treatment mixture 20. FIG. 2 is a sectional view of the body of cattail blossom 10 which shows a multitude of seeds 15 that are tightly packed around central stem 12. The sectional view of the body of cattail blossom 10 shown in FIG. 2 has been partially cut away to also expose central stem 12.

When cattail blossom 10 is sufficiently dry, it will burst or disintegrate to discharge large numbers of seeds such as seeds 15. Seeds 15 each include a seed portion and bristly, fiber portion that aids in wind dispersal. When seeds 15 are released, cattail blossom 10 completely disintegrates and is no longer useful as a decorative item.

The tightly packed seeds 15 of cattail blossom 10 shown in FIG. 2 do not comprise a completely solid mass but comprise a porous mass having a porous surface. Accordingly, it is possible for a liquid agent having a relatively low viscosity to penetrate the surface of cattail blossom 10 and replace the air present between the packed seeds 15. When an adhesive agent is introduced into cattail blossom 10 having a relatively low viscosity and low surface tension, the adhesive agent will penetrate the body of blossom 10 and bind together the fibers of seeds 15 to form a highly stable composite material that will remain intact.

The preferred method for treating cattail blossom 10 so that it will remain intact and not burst for a long period of time includes the following steps. 1. Obtain a dry cattail such as cattail blossom 10 that has not burst and which is still intact. 2. Thoroughly mix a treatment mixture of an adhesive agent and a thinning agent. The treatment mixture preferably includes approximately between 35% and 65% adhesive agent and between 35% and 65% thinner. Most preferably, the adhesive selected is LIQUID NAILS® construction adhesive for subfloors and decks which is marketed by the Glidden Company of Cleveland, Ohio and the thinning agent is preferably mineral spirits paint thinner. The inventor has found that a highly effective mixture is a mixture of preferably LIQUID NAILS® construction adhesive and 50% mineral spirits thinner. The inventor has also found that it is preferable to maintain this treatment mixture at a warm temperature approximately between 80° F. and 100° F. Generally, an effective amount of thinning agent has been used and a proper temperature has been used if the resulting mixture readily soaks into cattail 10 when cattail 10 is submerged in the resulting mixture. Moreover, if the treatment mixture is maintained at a lower temperature then more thinning agent may be needed. 3. Submerge cattail blossom 10 while it is in a substantially vertical orientation as shown in FIG. 1 into treatment mixture 20 until cattail blossom 10 is saturated. Cattail blossom 10 stops producing air bubbles when it is saturated and treatment mixture 20 is no longer soaking into cattail blossom 10. 4. Hang cattail blossom 10 in the vertical orientation as shown in FIG. 1 to allow it to drain and dry.

LIQUID NAILS® construction adhesive is the preferred adhesive agent. It generally consists of various petroleum distillates,. polymers and other constituents such as Calcium carbonate dust. LIQUID NAILS® construction adhesive can generally include by weight between 40% to 50% Calcium carbonate dust, approximately 3% clay, 20% to 25% petroleum distillates such as Naphtha, Butane, Pentane and Acetone, approximately 30% polymers such as steam cracked polymers with light steam cracked petroleum naphtha and butadiene, styrene and divinylbenzene polymer and about 7% resin acids & rosin acids and esters with glycerol. The LIQUID NAILS® construction adhesive that the inventor has found to yield the best results when mixed an approximately equal volume of mineral spirits thinner includes the following ingredients: Petroleum distillates, hydrotreated heavy Naphthenic (64742-52-5), steam cracked polymers with light steam cracked petroleum Naphtha (68410-16-2), Benzene, Ethenyl-polymer with 1,3 Butadiene (9003-55-8), Benzene, 1,3 Diethenyl-polymer with 1,3 Butadiene and Ethenylbenzene (26471-454), carbonic acid Calcium salt, Kaolin (1332-58-7), Naphtha solvent, Light Aliphatic (64742-89-8), Quartz (14808-60-7) and Cyclohexane (110-82-7).

The inventor recognizes that it may be possible to replace the above described mixture with a mixture including other adhesives, bonding agents, waxes or epoxies that may be mixed with an appropriate thinning agent. It is, however, important that adhesive mixture 20 used for treating cattail blossoms such as cattail blossom 10 have a relatively low surface tension or a relatively low viscosity so that it can soak into cattail blossom 10 and thereby saturate or impregnate blossom 10. It is also important that adhesive mixture 20 have a binding strength sufficient to prevent cattail blossom 10 from bursting. The end result of the above described process is a cattail blossom that has a natural appearance but that is also impregnated with an adhesive agent such that the seeds of the body of the cattail blossom are bonded together to form a substantially solid, stable mass. A cattail blossom that has been treated with the above described process will remain intact for an indefinite period of time.

As can be readily understood by the skilled reader, the above described process can be practiced with large quantities of cattails in either a batch or continuous process. Cattails which have been treated as described above can be decorated or painted and displayed indefinitely.

Obviously, in view of the method described above, numerous modifications and variations of the preferred method disclosed herein are possible and will occur to those skilled in the art in view of this description. It is to be understood that while certain forms of this invention process have been illustrated and described, it is not limited thereto, except in so far as such limitations are included in the following claims. Having thus described the invention.

What is claimed as new and desired to be secured by Letters Patent is as follows:

1. A method for treating a cattail blossom to prevent bursting and dispersal of the seeds thereof comprising the following steps;
   (a) obtaining a dry cattail having a cattail blossom that is intact,
   (b) obtaining a treatment mixture comprising an adhesive and an effective amount of a thinning agent to enable the treatment mixture to soak into the cattail blossom,
   (c) submerging the cattail blossom of the cattail in the treatment mixture of step (b) until the cattail blossom is substantially saturated, and
   (d) drying the cattail.

2. The method of claim one, wherein the treatment mixture comprises an adhesive agent and a mineral spirits thinner.

3. The method of claim one, wherein the adhesive agent is chosen from the group consisting essentially of adhesive, epoxy, glue or wax.

4. The method of claim one, wherein the treatment mixture comprises:
   (a) an adhesive which comprises a carbonate, a polymer, a petroleum distillate and an acid selected from the group consisting essentially of a resin acid and a rosin acid, and
   (b) an effective amount of a thinning agent to enable the resulting treatment mixture to soak into the cattail blossom.

5. The method of claim one, wherein the treatment mixture comprises between approximately 35% and 65% mineral spirits.

6. The method of claim one, wherein the treatment mixture comprises approximately 50% mineral spirits.

7. The method of claim one, wherein the treatment mixture is maintained at a temperature of between approximately 80° F. and 100° F.

8. The method of claim one, wherein the treatment mixture comprises:
   (a) an adhesive which comprises a carbonate, a polymer, a petroleum distillate and an acid selected from the group consisting essentially of a resin acid and a rosin acid,
   (b) an effective amount of a thinning agent to enable the resulting treatment mixture to soak into the cattail blossom, and
   (c) wherein the treatment mixture is maintained at a temperature of between approximately 80° F. and 100° F.

9. A method for treating a cattail blossom to prevent bursting and dispersal of the seeds thereof comprising the following steps;
   (a) obtaining a dry cattail having a cattail blossom that is intact,
   (b) obtaining a treatment mixture comprising an adhesive and a thinning agent, the adhesive comprising a carbonate, a polymer, a petroleum distillate and an acid selected from the group consisting essentially of a resin acid and a rosin acid, the thinning agent in an amount sufficient to enable the resulting treatment mixture to soak into the cattail blossom,
   (c) submerging the cattail blossom of the cattail in the treatment mixture of step (b) until it is substantially saturated, and
   (d) drying the cattail.

10. The method of claim nine, wherein the treatment mixture comprises between approximately 35% and 65% mineral spirits.

11. The method of claim nine, wherein the treatment mixture comprises approximately 50% mineral spirits.

12. The method of claim ten, wherein the treatment mixture is maintained at a temperature of between approximately 80° F. and 100° F.

* * * * *